(12) United States Patent
Sinha

(10) Patent No.: US 7,963,165 B2
(45) Date of Patent: Jun. 21, 2011

(54) NON-CONTACT FEATURE DETECTION USING ULTRASONIC LAMB WAVES

(75) Inventor: Dipen N. Sinha, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 167 days.

(21) Appl. No.: 11/861,229

(22) Filed: Sep. 25, 2007

(65) Prior Publication Data

US 2009/0078049 A1 Mar. 26, 2009

(51) Int. Cl.
*G01N 29/34* (2006.01)
(52) U.S. Cl. ............... 73/623; 73/596; 73/597; 73/649; 73/655
(58) Field of Classification Search .............. 73/596, 73/600, 601, 622, 623, 627, 628, 645, 646, 73/649, 655, 657, 598, 597; 367/87, 92
See application file for complete search history.

(56) References Cited

U.S. PATENT DOCUMENTS

| | | | |
|---|---|---|---|
| 4,063,457 A * | 12/1977 | Zekulin et al. ............. 73/290 V |
| 4,954,997 A * | 9/1990 | Dieulesaint et al. ........... 367/13 |
| 5,587,534 A | 12/1996 | McColskey et al. |
| 6,148,672 A | 11/2000 | Cawley et al. |
| 6,186,004 B1 | 2/2001 | Kaduchak et al. |
| 6,234,023 B1 * | 5/2001 | Collins et al. .................. 73/597 |
| 6,644,119 B1 * | 11/2003 | Sinha ............................. 73/579 |
| 6,680,994 B2 * | 1/2004 | Jones et al. .................... 376/250 |
| 6,925,870 B2 * | 8/2005 | Pappas et al. ............... 73/290 V |
| 6,938,488 B2 * | 9/2005 | Diaz et al. ....................... 73/597 |
| 7,114,390 B2 * | 10/2006 | Lizon et al. ................. 73/290 V |

OTHER PUBLICATIONS

International Search Report for PCT/US08/11031, International Searching Authority, Nov. 25, 2008, p. 1-8.

* cited by examiner

*Primary Examiner* — J M Saint Surin
(74) *Attorney, Agent, or Firm* — Samual M. Freund; Cochran Freund & Young LLC; Meredith H. Schoenfeld

(57) ABSTRACT

Apparatus and method for non-contact ultrasonic detection of features on or within the walls of hollow pipes are described. An air-coupled, high-power ultrasonic transducer for generating guided waves in the pipe wall, and a high-sensitivity, air-coupled transducer for detecting these waves, are disposed at a distance apart and at chosen angle with respect to the surface of the pipe, either inside of or outside of the pipe. Measurements may be made in reflection or transmission modes depending on the relative position of the transducers and the pipe. Data are taken by sweeping the frequency of the incident ultrasonic waves, using a tracking narrow-band filter to reduce detected noise, and transforming the frequency domain data into the time domain using fast Fourier transformation, if required.

24 Claims, 10 Drawing Sheets

FIG. 4A
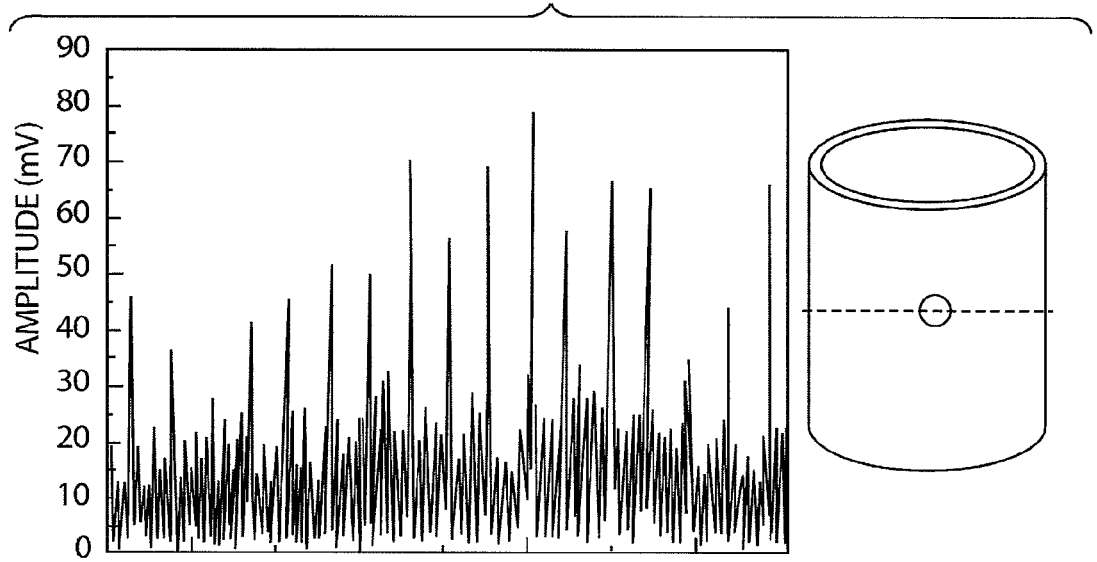
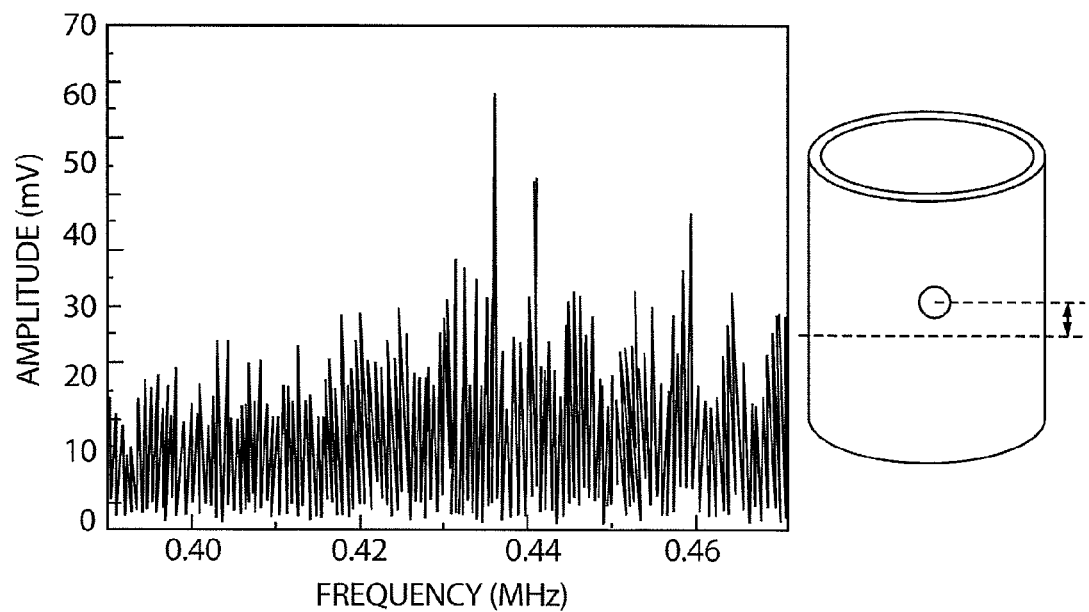
FIG. 4B

NON-CONTACT FEATURE DETECTION USING ULTRASONIC LAMB WAVES

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to apparatus and method for detecting features on or within pipe walls and, more particularly, to the non-contact (stand-off) detection of features on or within pipe walls.

BACKGROUND OF THE INVENTION

The national gas infrastructure of the United States is both vast and varied. Materials used in the construction of pipeline, their age and their location are major variables in maintaining pipeline integrity. The ability to inexpensively and efficiently monitor and assess pipeline integrity and status may provide improved means for service-life prediction and defect detection to ensure operational reliability. Existing techniques do not work well, and the expense for using eddy currents, as an example, is approximately $1 M per 100 mile of pipe, and can only detect gross defects in the pipes. Visual inspection using cameras provides little information concerning the integrity of the pipeline.

The most common causes of pipeline failure in North America include mechanical damage; that is, denting or gouging of the pipeline caused by workers (digging using backhoes, as an example), and natural corrosion over time. In many cases, the pipes will fail under load unless defects are detected in a timely manner. In other situations, they may remain undetected, with the local damage acting as sites for further corrosion or cracking, and potentially leading to a delayed failure, such as an explosion.

Presently, visual inspections employing video cameras are the primary means for inspection of the interiors of natural gas pipelines. However, such procedures do not permit one to view damage to the outside surface of pipe. Eddy currents generated by strong magnets placed close to the inner surface of the pipe are also used to detect features. However, since natural gas pipelines are made of steel, moving such magnets through the pipe may be difficult due to the Eddy current braking effect. Additionally, because of the close proximity of the magnets to the interior of the pipe, the sensor elements may scrape the inner wall of the pipe, thereby fouling the sensor. The interiors of the pipes must therefore be cleaned with metal brushes before this procedure is utilized. The Magnetic flux leakage (MFL) technique suffers from the same difficulties as the eddy current method.

The United States has over 2 million miles of gas pipelines. Of interest is a sensing system that can be mounted on a 'pig' (a device inserted into a pipeline for inspection or cleaning purposes) which travels through the inside of a natural gas pipeline and is suitable for detection of wall defects such as corrosion pits on both the inside and the outside of pipe. It is of importance that the sensing system does not have rotating or otherwise moving parts in order to simplify the design, make it easier to maintain and also to conserve battery power for longer inspections.

In U.S. Pat. No. 6,186,004 for "Apparatus And Method For Remote, Noninvasive Characterization Of Structures And Fluids Inside Containers" which issued to Gregory Kaduchack et al. on Feb. 13, 2001, an apparatus and method for remote, non-contact evaluation of structures and containers at large distances (on the order of several meters) in air is described. The invention utilizes an air-coupled, parametric acoustic array to excite resonance vibrations of elastic, fluid-filled vessels and structural members, where a nonlinear mixing process in the air medium transforms highly directional, narrow beamwidth higher acoustic frequencies into lower acoustic frequencies suitable for vibrational excitation of common structures. Vibrations were readily detected using a laser vibrometer in a fixed position relative to the acoustic array. Interior fluid characterization was achieved by analyzing the propagation of the generated guided waves (for example, the lowest-order generalized antisymmetric Lamb wave, $a_0$) which is guided by the circumference of the container. The $a_0$ Lamb wave is in a class of guided waves which exhibit strong flexural vibrations near the resonance frequency of the container. It should be pointed out that the parametric array requires a minimum distance from the acoustic source of several wavelengths in air before it can generate the lower frequency sound wave, and thus cannot be fitted inside of typical natural gas pipelines that can range from 4 in. to 18 in. in diameter. Moreover, the mixing process is intended to produce frequencies less than about 40 kHz.

Pulse-echo, time-of-flight procedures have been used to determine sound propagation through materials. A narrow electrical pulse is used to excite a transducer which generates sound waves in an object such as a plate. The pulse propagates through the object and is detected by either the same transducer or by another. By determining the travel time over a known distance within the object, the sound velocity may be determined. A narrow pulse has high-frequency content requiring a high-bandwidth amplifier to detect the signals from the receiving transducer. Unfortunately, this exposes the measurement to the entire bandwidth of the amplifier. Further, typical pulse-echo measurements require transducer excitation voltages between 300 V and 500 V and much signal averaging or fast frequency chirp correlation techniques to make meaningful, air-coupled signal measurements.

SUMMARY OF THE INVENTION

Accordingly, it is an object of the present invention to provide a non-contact (stand-off) apparatus and method for locating features on or within pipe walls.

Another object of the invention is to provide an apparatus and method for locating features on or within pipe walls without the use of magnets either permanent or electrically generated.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for non-contact detection of features in or on the wall of a hollow pipe having a longitudinal axis, the wall having an inner surface, hereof, includes: an air-coupled transmitting transducer disposed within the hollow pipe for generating ultrasonic waves at a first chosen angle to the normal of the inner surface of the wall, at a chosen first distance therefrom, and at a chosen longitudinal distance along the axis; a sweep generator for exciting the air-coupled transmitting transducer over a selected frequency range, whereby Lamb waves are generated in the wall of the pipe; an air-coupled receiving transducer disposed within the hollow pipe at the same longitudinal position as the transmitting transducer, at a chosen angle to the inner to the normal to the inner surface of the wall and at a second chosen distance from the inner surface, for receiving ultrasonic waves emitted by the inner surface of the wall, the receiving transducer producing an electrical signal in response to the ultrasonic waves received thereby; a narrow-band tracking filter for receiving the electrical signal from the receiving transducer at the excitation frequency in the selected frequency range and generating a noise-filtered signal therefrom; and a signal processor for receiving the noise-filtered signal from the narrow-band tracking filter and producing a signal containing amplitude and phase information from the Lamb waves in the frequency domain.

In another aspect of the present invention and in accordance with its objects and purposes, the method for non-contact detection of features in or on the wall of a hollow pipe having a longitudinal axis, the wall having an inner surface, hereof, including: generating ultrasonic waves having a chosen frequency in a selected frequency range, at a chosen angle to the normal to the inner surface of the wall and from a first chosen distance therefrom, and at a chosen longitudinal distance along the axis, whereby Lamb waves are generated in the wall of the pipe; sweeping the generated ultrasonic waves over the selected frequency range; detecting ultrasonic waves emitted by the inner surface of the wall of the pipe at a second chosen distance therefrom and at a second chosen angle to the normal of the inner surface; producing a signal from the detected ultrasonic waves; and generating a narrow-band, noise-filtered signal at each frequency from the signal; whereby a signal containing amplitude and phase information from the Lamb waves is generated in the frequency domain.

In still another aspect of the present invention and in accordance with its objects and purposes, the apparatus for non-contact detection of features in or on the wall of a hollow pipe having a longitudinal axis, the wall having an outer surface, hereof, including: an air-coupled transmitting transducer disposed outside of the hollow pipe for generating ultrasonic waves at a first chosen angle to the normal to the outer surface of the wall, at a chosen first distance therefrom and at a chosen longitudinal distance along the axis; a sweep generator for exciting the air-coupled transmitting transducer over a selected frequency range, whereby Lamb waves are generated in the wall of the pipe; an air-coupled receiving transducer disposed outside of the hollow pipe at the same longitudinal position as the transmitting transducer, at a second chosen angle to the normal to the outer surface of the wall and at a second chosen distance from the outer surface, for receiving ultrasonic waves emitted by the outer surface of the wall, the receiving transducer producing an electrical signal in response to the ultrasonic waves received thereby; a narrow-band tracking filter for receiving the electrical signal from the receiving transducer at the excitation frequency in the selected frequency range and generating a noise-filtered signal therefrom; and a signal processor for receiving the noise-filtered signal from the narrow-band tracking filter and producing a signal containing amplitude and phase information from the Lamb waves in the frequency domain.

In yet another aspect of the present invention and in accordance with its objects and purposes, the method for non-contact detection of features in or on the wall of a hollow pipe having a longitudinal axis, the wall having an outer surface, hereof, comprising: generating ultrasonic waves having a chosen frequency in a selected frequency range at a first chosen angle to the normal to the outer surface of the wall from a first chosen distance therefrom, and at a chosen longitudinal distance along the axis, whereby Lamb waves are generated in the wall of the pipe; sweeping the generated ultrasonic waves over the selected frequency range; detecting ultrasonic waves emitted by the outer surface of the wall of the pipe at a second chosen angle to the normal to the outer surface and at a second chosen distance therefrom; producing a signal from the detected ultrasonic waves; and generating a narrow-band, noise-filtered signal at each frequency from the signal; whereby a signal containing amplitude and phase information from the Lamb waves is generated in the frequency domain.

Benefits and advantages of the present invention include, but are not limited to, providing apparatus and method for non-contact detection of features located on the outside of a pipe from the inside thereof, and vice versa, and defects located within the pipe walls. The present invention is anticipated to find use in nuclear power plants, exhaust chutes, pipelines carrying hot gases, and for hot pipes, as might be found in refineries such that a non-contact approach is required, and for detecting coking and other deposit formation inside pipes without becoming fouled by these deposits, to name a few examples. Since the present detection system does not employ large magnets, magnetic drag of the system through pipes is not a problem and a sensor transporter ('pig') may be operated using batteries, because of the low power consumption of the transducers and the processing circuit. Additionally, although the transducers are fixed in place, the Lamb waves travel around the circumference of the pipe and detect defects in their path without requiring that the transducers scan the surface as required in many existing techniques.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of one embodiment of the apparatus of the present invention showing a hollow pipe having a transmitting transducer and a receiving transducer located on opposite sides of the inside cylindrical surface thereof; a sweep generator for driving the transmitting transducer over a selected range of sine-wave frequencies; low-pass filter circuitry for processing amplitude and phase information from the receiving transducer; a digital signal processor for further processing amplitude and phase information; apparatus for controlling the electronic circuitry; and apparatus for displaying and recording the resulting information, while

FIG. 2A is a graph of the amplitude of the detected Lamb waves as a function of frequency, the sharp lines corresponding to standing Lamb waves propagating along the surface of an aluminum pipe, the transmitting and detecting air-coupled transducers being located on the outside surface of the pipe, while FIG. 2B is the amplitude as a function of time for the Fourier transformed data of FIG. 2A, the equidistant peaks (in time) showing the sound pulse traveling around the circumference of the pipe multiple times and slowly decaying during this process.

for emitted Lamb waves from a hollow pipe away from any defects, and is similar to the graph shown in FIG. 2 hereof except that the data is taken using transducers disposed on the inside of the hollow pipe; while

FIG. 4A is a graph of amplitude as a function of frequency for transducers disposed at a longitudinal location that is approximately in line with the location of a defect in the exterior of the wall of the cylinder, whereas the transducers are located interior thereto, while FIG. 4B is a graph of the amplitude as a function of frequency for internal transducers disposed away from the location of the defect, scattering from the defect along the path of the circulating Lamb waves generating standing waves which are not observed when the transducers are away from this location.

FIG. 5C is a graph of the FFT as a function of time for a cylindrical rotation of 40°, again in the plane of the defect, the latter two rotations generating an additional peak at between 200 and 300 µs which changes position as the cylinder is rotated about its longitudinal axis of symmetry.

FIG. 7B showing a curve for a defect having a depth of 20% of the wall thickness on the outside thereof; FIG. 7C showing a curve for a defect having a depth of 50% on the outside thereof; and FIG. 7D showing a curve for a defect having a depth of 80% on the outside thereof, the transducers being located 180° apart as shown in FIG. 5 hereof and facing the inside surface of the cylinder, with the defects located on the outside wall at approximately 90° from either transducer.

DETAILED DESCRIPTION OF THE INVENTION

Figure 1A:
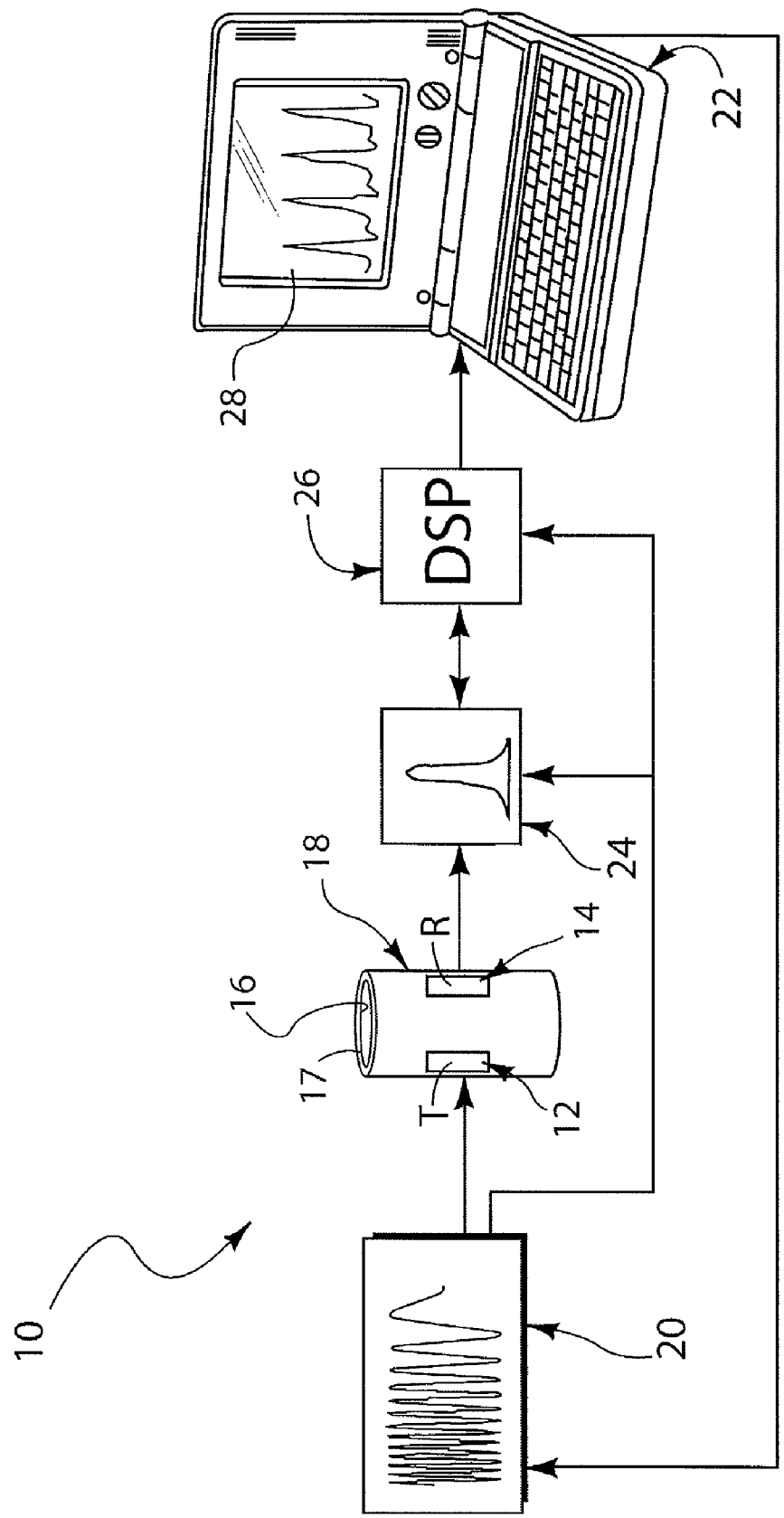

Briefly, the present invention includes apparatus and method for non-contact ultrasonic detection of features on or within pipe walls. An air-coupled, high-power ultrasonic transducer for generating guided waves (for example, Lamb waves) in the pipe wall, and a high-sensitivity, air-coupled transducer for detecting these waves, are disposed at a distance apart and at chosen angle, which depends on the thickness of the pipe being investigated (generally between about 4° and about 10° for most practical applications for natural gas pipes (between 0.1 in. and 0.3 in. thick), the frequency range of the transducers, and the distance with respect to the surface of the pipe surface, since these parameters determine which Lamb wave mode is generated. To avoid the effects of corrosion, pitting or dirt interior to the pipe, for steel gas-carrying pipes, a distance from the surface of the pipe of greater than 2 cm is anticipated to be generally suitable. One of the objects of the present invention is to determine defects in a non-contact manner from the opposite surface of the pipe from the defect. The invention has been demonstrated to be completely reversible as to whether the transducers are on the inside or the outside of the pipe. It should be mentioned that the angles the output of the transducers make with the surface of the pipe becomes less important the further the transducers are located from the surface; at 2 cm, perpendicular orientation is near optimal.

The waves are guided by the two surfaces of the wall of the pipe (or other solid), and the propagation velocity is related to the frequency used to excite the waves. By changing the angle of the transducers with the surface of the wall, one can excite different propagation modes. It should be mentioned that the angle of the impinging ultrasonic beam is between about 4° and 10° from the normal to the surface in order for Lamb waves to be generated in the wall of the pipe. This defines the direction of propagation of the Lamb waves to be away from the transmitter and toward the receiver. The angle for detecting such waves emanating from the pipe surface is likewise between 4° and 10° from the normal to the surface of the pipe, but in the direction of the incoming waves launched from the transmitter. In practice, the angles for the transmitting transducer and the receiving transducer may be made the same. No Lamb waves were observed for angles close to 0° to the normal.

It should be mentioned that these angles obtain for air or gases, such as natural gas under pressure, for which the speed of sound does not change appreciably. However, the present invention may also be utilized for liquids, such as crude oil or water for which the angles will be larger (~40°).

Varying the distance between the transducers and the surface of the pipe may result in:

(1) A change in the path length for the propagation of the guided (Lamb) wave (and also the path in air) which may affect the time of arrival of the pulses (the time-domain data converted from the frequency sweep measurement which is equivalent to exciting the pipe with a pulse and observing the propagation of this pulse). The sound speed in air is different from that of the Lamb wave in the pipe wall and the effect will be a combined effect if both are changed simultaneously.

(2) A change in the spread in the beam pattern since sound from the transmitting transducer diverges slightly. As a result, there is a slight spread in the contact angle between the sound beam and the wall surface. The beam divergence also depends on the frequency; the higher the frequency, the narrower is the beam spread. A small beam spread may be beneficial because exact alignment is not required. For small spacings between the transducers and the wall surface the alignment is more important. However, for spacings greater than about 2 cm from the surface, beam alignment has not been found to be a problem.

(3) A decrease in the sound intensity as the separation between the transmitter and the wall surface increases, resulting in a weaker signal.

In accordance with one embodiment of the present invention, the angle between the transducers is fixed at a chosen value, and the excitation frequency is varied, thereby also changing the propagation characteristics. As a result of the large impedance mismatch between air and the metal wall, more than 99.998% of the excitation sound energy is reflected, and a small fraction is converted into guided waves. These waves propagate through the pipe wall and a small amount of energy is reradiated and detected by the detecting transducer which also suffers from losses due to impedance mismatch. Therefore, means for extracting small signal-to-noise ratio signals from the detected signal are provided.

Pulse echo technology cannot provide adequate signal-to-noise ratio for such measurements without using very high voltage for transducer excitation followed by much signal averaging. It is possible to obtain the same time-domain information but from a frequency domain technique such that the noise bandwidth can be significantly reduced (orders of magnitude). An advantage of using a time-domain procedure derived from a frequency sweep is the ability to achieve much higher signal-to-noise ratio information using much lower excitation voltages. As will be discussed in more detail hereinbelow, measurement at each frequency between a start and stop frequency is made through a narrow band (~100 Hz) tracking filter restricting the received noise to a narrow, sliding frequency window throughout the entire frequency sweep range. There are many procedures for implementing such a tracking filter in practice and the electronics to do so are commercially available; for example, a vector network analyzer. In what follows, the term tracking filter will be used as representative of a filter which is effective at the various sine-wave frequencies employed, and for which one embodiment is described in FIG. 1B hereof. By contrast, the noise window for pulse-echo measurements would be the equivalent of the entire bandwidth of the transmitted pulse. Thus, for a 1 MHz bandwidth pulse-echo measurement, the swept frequency technique can provide a signal-to-noise ratio improvement of approximately 4 orders of magnitude (700 kHz/100 Hz) when comparing the filter widths.

The present swept frequency technique permits a mere 5 V excitation signal to generate high-quality measurements, thus extending the life of the broadband transducers from damage due to high voltages and heating. High voltages are also not safe in an environment that has combustible gases at high pressures. Although the amplitude and phase of the signals generated as the guided wave propagates through a metal plate are subjected to signal-to-noise ratio enhancement, the frequency spectrum produced may contain significant noise. However, upon transformation of the data into the time domain using a Fast Fourier Transform, the data appear to be greatly improved.

It is intended that the present invention be adapted for use with natural gas pipe lines, both empty and flowing. The measurements discussed in the EXAMPLES hereinbelow, however, have been made using ambient air which represents the most difficult measurements because the sound coupling to the wall at ambient pressure is the least. Higher gas pressures improve coupling such that more energy is coupled into the pipe, thereby making the signals stronger. There is some data from one transducer manufacturer that shows that this coupling saturates (or goes up asymptotically only) beyond 50 psi. Typical gas pressure in the pipeline is in the hundreds of psi. Heat is not generally a problem because there are transducers available that can operate at temperatures in hundreds of degrees. The Curie temperature of the piezoelectric material which is almost 1000° C. for quartz or Lithium Niobate, determines the upper temperature limit since operating below about one-half the Curie point is considered to be safe. For crude oil, at any temperature for which the oil is molten, the coupling is orders of magnitude better than for gases or for air. Commercially available transducers that continuously operate to 1000° F. may be purchased.

In accordance with the teachings of the present invention, measurements may be made in reflection or transmission modes depending on the relative position of the transducers and the pipe. In the reflection mode, both transmitter and receiver are disposed on the same surface of the pipe. For example, if a "pig" is employed, all instrumentation is located inside the pipe. If the pipe is located underground, it is not possible to make measurements in the transmission mode since one of the transducers would be located on the opposite surface of the wall, unless the pipe were freed of its enclosing material. For transmission measurements, sound transmission through the wall is measured. This is useful for spot checking wall thickness when there is access to the outer wall.

Data are obtained by sweeping the frequency of the incident ultrasonic waves, using a tracking narrow-band filter to reduce detected noise, and transforming the frequency domain data into the time domain using complex, fast Fourier transformation. The range of operation is anticipated to be between about 50 kHz and about 700 kHz. The actual frequency range employed depends on the pipe wall thickness in that the greater the wall thickness, smaller the frequency required. The dispersion curve (sound speed as a function of frequency times the thickness) for a given material, is universal. Electronically, higher frequency ranges produce better signal-to noise ratios. Therefore, if traditional pulse echo measurements are compared with the data derived from a frequency sweep measurement over a certain bandwidth and sweep time, the quantity of process gain, which may be of the order of 70 dB for a 10 s sweep time for an approximately 700 KHz sweep and a 500 Hz band pass tracking filter, is reflected in the improvement of the signal-to-noise ratio.

Reference will now be made in detail to the present embodiments of the invention, examples of which are illustrated in the accompanying drawings. In the Figures, similar structure will be identified using identical reference characters. Turning now to FIG. 1A, a schematic representation of one embodiment, 10, of the swept frequency apparatus of the present invention is illustrated. Transmitting transducer, 12, and receiving transducer, 14, are gas matrix air-coupled transducers obtained from Ultran Laboratories in Pennsylvania. Transducers 12 and 14 are broadband transducers (frequency range: 300 kHz-700 kHz) having high power output and very sensitive reception, and are intended to be illustrated in FIG. 1 as being disposed about 2 cm from the inside surface, 16, of wall, 17, of hollow pipe, 18, at about 180° apart in the reflection mode. Sweep generator, 20, controlled by microprocessor, 22, drives transmitting transducer 12 through a selected frequency range of sine waves. It should be mentioned that other periodic waveforms could be employed (for example, square waves and triangle waves) since the higher harmonics contained in such waves would not be detected by the tracking circuitry described hereinbelow. Radiated signals received by receiving transducer 14, are directed through narrow-band-pass filter circuitry, 24, to digital signal processor electronics, 26, where it is processed, including conversion of the frequency spectrum to the time domain by FFT (Fast Fourier Transform), and displayed by display apparatus, 28. DSP 26 may also carry out various mathematical operations to process the data further, if desired.

To recover information in a frequency sweep measurement one needs to restrict the noise to a very narrow bandwidth. Further, amplitude and phase measurements must be made within this narrow bandwidth. A complex fast Fourier transform using both amplitude and phase information is then made to recover the time-domain data with high signal-tonoise ratio. In principle, the measurements are made through a narrow band pass filter that effectively tracks the frequency sweep.

The signal (sine-wave) applied to transmitter transducer is impressed in the pipe and is detected by the receiver transducer, after traveling a certain distance in the pipe, thereby generating a time delay (phase delay) relative to the impressed signal, when compared with the original input signal (at 0°) and at its phase-shifted value of 90° (known as signals in quadrature). The received signal is multiplied with signals in quadrature and the resultant signals passed through low-pass filters to remove extraneous higher frequency signals. The cutoff frequency of the low-pass filter is chosen at a desired fixed frequency, such as 100 Hz for all sweep frequencies, the apparatus hereof in effect using fixed-frequency, low-pass filters to generate a tracking, low band-pass filter having a desired bandwidth.

Figure 1B:
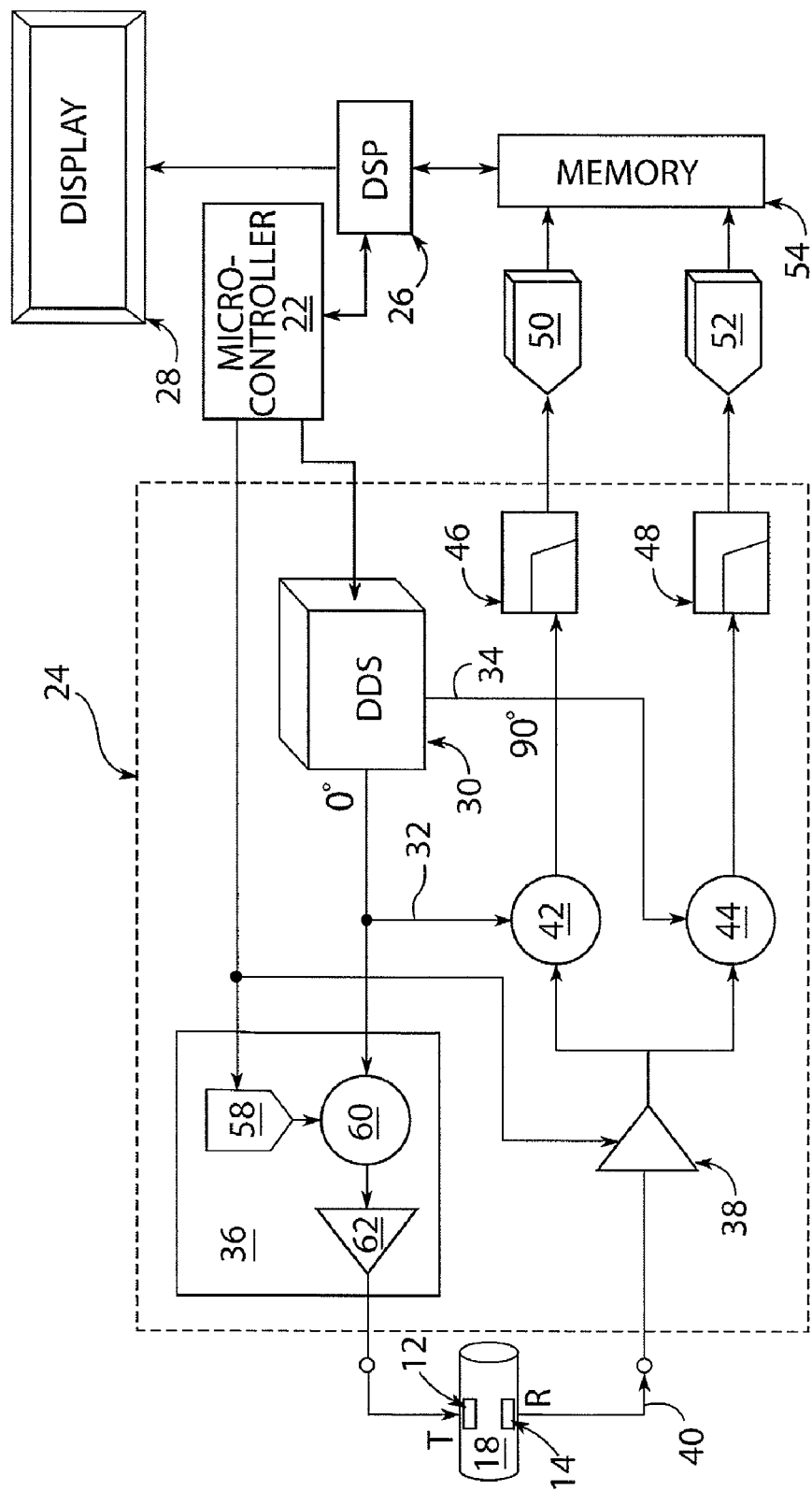
FIG. 1B shows one embodiment of some of the details of the components shown in FIG. 1A, hereof.

Turning now to FIG. 1B, the sweep measurement requires the simultaneous determination of both phase and amplitude of the received signal within a narrow frequency band. This measurement is made at every frequency as the frequency is varied between selected limits (low and high values). Microcontroller/processor 22 controls direct digital synthesizer (DDS), 30, having quadrature output (sine wave having a desired frequency at 0°, 32, and 90°, 34, of phase relationship with one another), programmable gain amplifier, 36, for driving transmitter transducer 12, inside pipe 18 and variable gain amplifier, 38, for amplifying received signal, 40, from receiver transducer 14. Controller 22 causes the frequency to be stepped between the chosen limits, and the measurements are made at each step. Two double-balanced mixers, 42 and 44, and two low-pass filters, 46 and 48, respectively, mix the quadrature signals from DDS 30 with the output from amplifier 38 and filter the high frequencies. The filtered signals are directed to analog-to-digital converters (ADC), 50 and 52, respectively and stored in memory, 54. DSP 26 processes the stored signals which may be displayed by display 28.

As stated hereinabove, microcontroller 22 is programmed to communicate with DDS 30 to generate two sine waves having the same frequency and a 90° phase difference between therebetween. The 0° signal is directed to programmable gain amplifier 36, the gain of which is derived from a gain value (DC voltage signal) from 8-bit digital-to-analog converter (DAC), 58, and is then multiplied, 60, with the sine wave signal from DDS 30, to produce a desired signal amplitude. This signal goes through power amplifier, 62, to drive transmitter (T) transducer 12. The signal from receiver (R) transducer 14 is amplified by a variable gain (user selectable gain) amplifier 38 and directed to simultaneously to mixers 42 and 44. Mixers 42 and 44 also receive in quadrature sine wave signals 32 and 34, respectively, and the resulting outputs are low-pass filtered, 46 and 48, respectively. The cut-off frequency of low pass filters 46 and 48 (for example, 100 Hz but variable to as much as 10 kHz for a faster sweep, if required) determines the narrow-frequency bandwidth of the measurement at a given frequency. The output of the low-pass filters are the Real (0 degree) and Imaginary (90 degree) signals of received signal 40. The output of low-pass filters 46 and 48 are then digitized by ADCs 50 and 52, respectively, converted to gain and phase values by DSP 26, and stored in memory. The resulting frequency spectrum may be displayed on display device 28. The DSP system may also convert the frequency spectrum to the time domain by FFT which may also be displayed. As stated, DSP 26 may perform various math operations to process the data further, as desired.

Typically, the frequency sweeps are performed with between 1024 and 8192 frequency steps between the two chosen frequency limits depending on the transducers used and the sample being tested. The described apparatus has the capability to produce and process a frequency range of 100 Hz to 10 MHz, and the number of frequency steps can be as large as 64,000 steps. Typical sweep times vary from 2 s to 10 s for a given measurement, but the electronics is not limited to that. The cut-off frequency of the low-pass filters can be increased to obtain higher speed, if desired. The excitation voltage for the transmitter transducer is typically less than 10 V, although the apparatus has the capability of generating higher voltages.

Three, 14-inch long pieces were cut from a single steel pipe (two pipe thicknesses: 0.188 in. and 0.254 in. were employed), and a single defect (1.5 inch in diameter) was inscribed on the outside surface of each of these pipe pieces with a numerical lathe so that the depth was uniform and parallel to the inner wall surface. The defects were placed at the center of the pipe so that interference from edge effects would be minimized. In addition to the pieces with defects, one pipe section was used as a reference to determine the response of a pipe without defects, and the uniformity of the signal.

Apparatus (not shown in FIG. 1) for permitting fine adjustments of transducer rotation and alignment with respect to the tube or pipe wall, and accurate positioning of the transducers at selected positions along the longitudinal symmetry axis (length) of the pipe and having 5° of freedom to align the transducers was provided. Tubes 18 having defects in their exterior walls were placed vertically such that the pipe could be raised or lowered. The tube could also be rotated along the vertical axis of symmetry. Transducers 12 and 14 were placed inside the pipe on opposite sides of the inside surface of pipe 18 with each facing the pipe surface. These can be adjusted so that angles between the sound beam and the inside surface can be selected, typically between about 4° and about 10° from the normal to the pipe surface. The front surface of the transducer was kept at approximately 2 cm (or greater) away from the inner pipe surface. The positions of the transducers were fixed and the pipe longitudinally moved by the transducers to scan the length (height) of the pipe to determine the presence of the defects.

As stated hereinabove, the transmitter transducer was driven by a voltage less than 10 V. The receiver transducer signal was analyzed, and recorded in real-time. This electronics has the capability to detect signal that is buried in noise by a factor of 1 part in 10 million. An electronics system using fast chirp and higher voltage excitation was also tested.

Figures 2A, 2B:
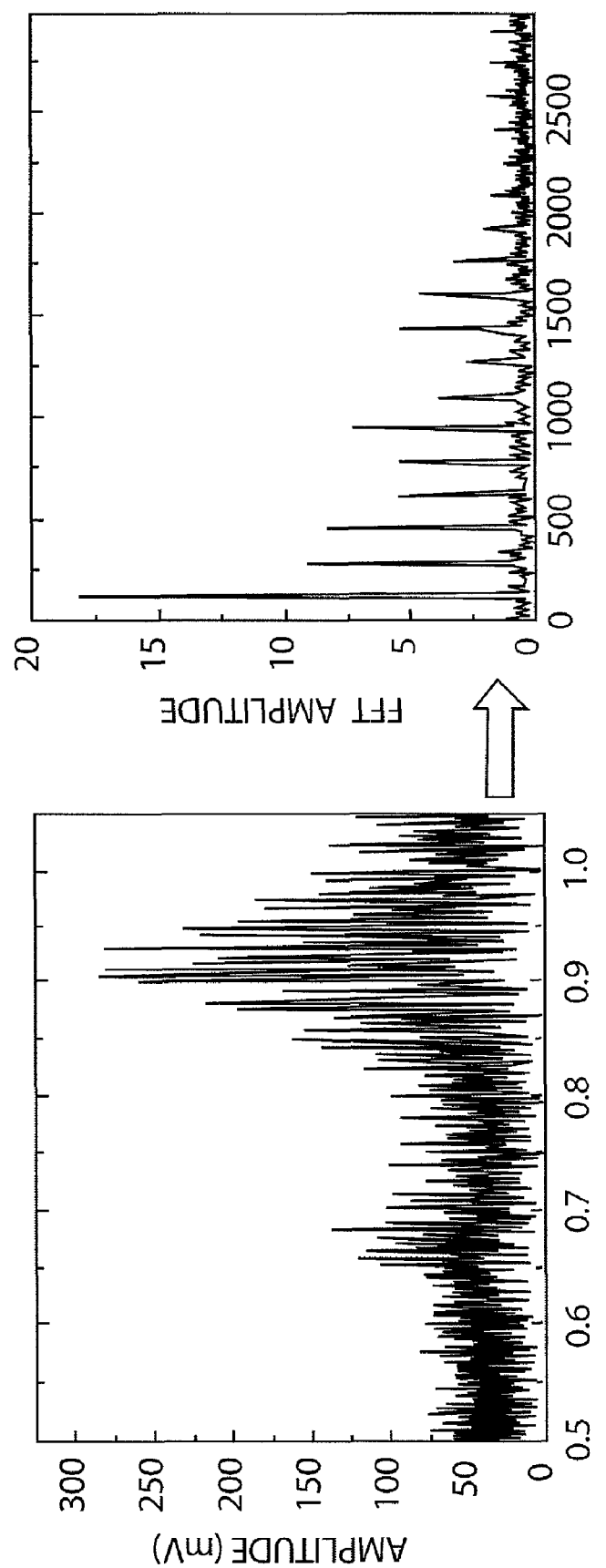

FIG. 2A is a graph of the amplitude of the detected Lamb waves as a function of frequency, the sharp lines corresponding to standing Lamb waves propagating along the surface of an aluminum pipe, the transmitting and detecting air-coupled transducers being located on the outside surface of the pipe, while FIG. 2B is the Fourier transformed data from FIG. 2A, the equidistant peaks (in time) showing that the sound pulse is traveling around the circumference of the pipe multiple times and slowly decaying during this process.

Figure 3A:
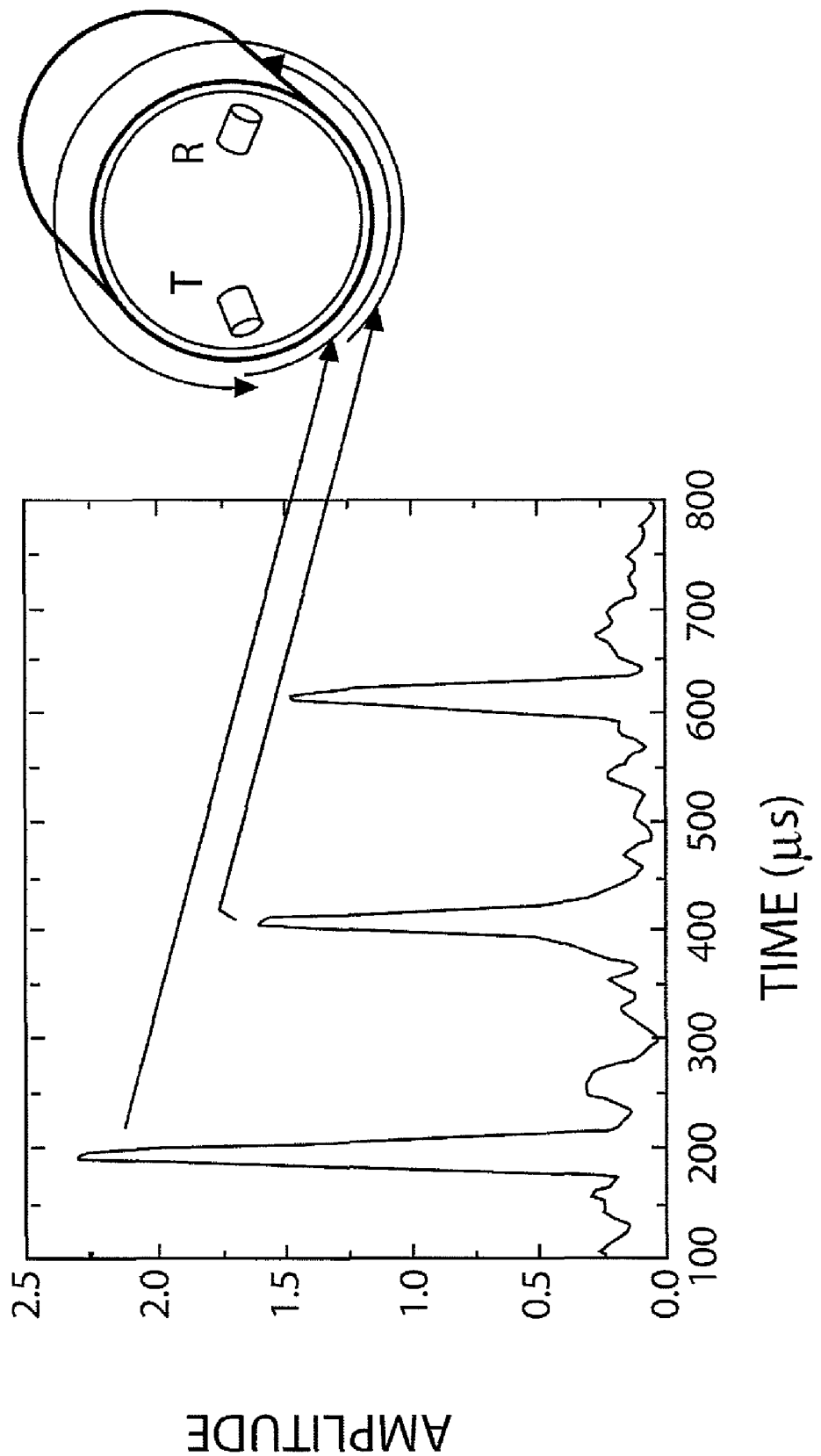
FIG. 3A is a graph of the signal amplitude as a function of time (time domain data derived from frequency sweep data)

Both forms of data (frequency domain experimental data and time-domain derived data) contain the same physical information. Because of the way in which the frequency-domain data are acquired, the noise content is small and is contained within a typically 100 Hz bandwidth, such high signal-to-noise ratio is not possible to obtain using traditional pulse-echo techniques. It is worth pointing out that this data was obtained using only a 9 V excitation. Even with a 300 V excitation and a commercial pulse-echo system, peaks cannot be observed in that data when compared with what is shown in FIG. 3A hereof. Multiple peaks in the time domain data are equivalent to a pulse of sound going around in circles along the circumference of the aluminum pipe (14 in. id×7 mm thick). The first peak shows the time a sound pulse takes to go from transmitter T to receiver R. This time includes the time of propagation through the air gap as well. The subsequent peaks represent the propagation time for a full circle. The speed of propagation can be determined easily from this data. When such pulses interact with any defect, it reflects and scatters the signal. Typically, this shows up as extra peaks, shift in peaks, splitting of peaks, and damping of peaks. Again, it should be pointed out that this time-domain (pulse equivalent) data are derived from the original frequency sweep measurements and are not direct measurements of pulse propagation.

Figure 3B:
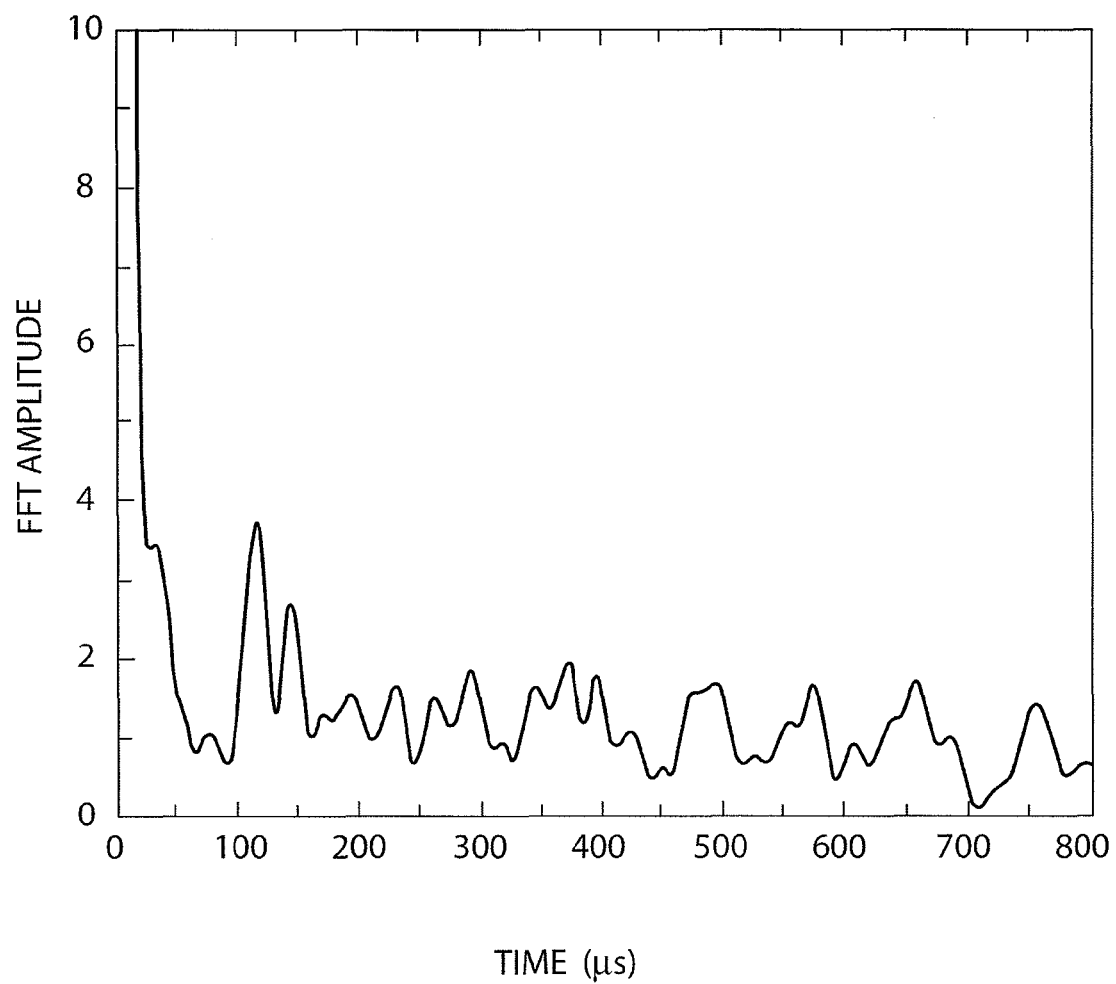
FIG. 3B is a graph of the amplitude as a function of time, where the amplitude data was processed without using phase information.

FIG. 3B shows the amplitude as a function of time where the amplitude data was processed without using the phase information, and clearly illustrates that no useful information is obtained from the measurements if the phase information is ignored.

Having generally described the invention, the following EXAMPLES provide additional detail:

EXAMPLE 1

FIG. 4A is a graph of amplitude as a function of frequency for transducers disposed at a longitudinal location that is approximately in line with the location of a defect in the exterior of the wall of the cylinder, whereas the transducers are located interior thereto, while FIG. 4B is a graph of the amplitude as a function of frequency for internal transducers disposed away from the location of the defect, the presence of the defect along the path of the circulating Lamb waves generating standing waves which are not observed when the transducers are away from this location.

EXAMPLE 2

Figure 5:
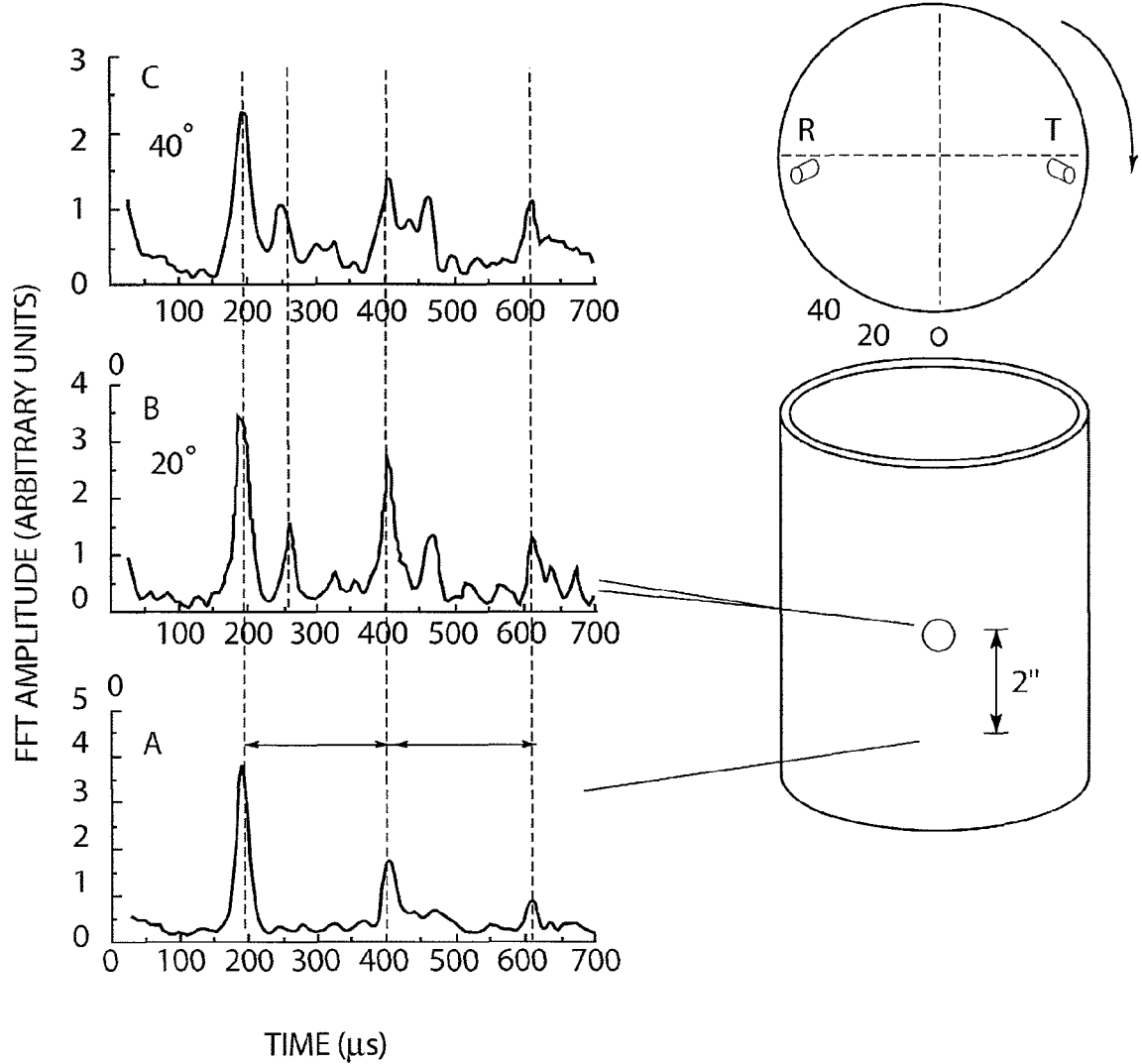
FIG. 5 shows graphs of amplitude as a function of time for transducers spaced approximately 180° apart in the plane of the defect (each transducer disposed about 90° along the inner surface of the pipe with respect to the defect defining the 0° position of the cylinder), with FIG. 5A showing the FFT amplitude as a function of time, taken about 2 in. from the defect location away along the longitudinal axis of the cylinder, FIG. 5B showing the FFT amplitude as a function of time for a cylinder rotation of 20° with the transducers held in a fixed location in the plane of the defect.

FIG. 5 shows graphs of amplitude as a function of time for transducers spaced approximately 180° apart in the plane of the defect (each transducer disposed about 90° along the inner surface of the pipe with respect to the defect defining the 0° position of the cylinder), with FIG. 5A showing the FFT amplitude as a function of time, taken about 2 in. away along the longitudinal axis of the cylinder from the defect location, FIG. 5B showing the FFT amplitude as a function of time for a cylinder rotation of 20° with the transducers held in a fixed location in the plane of the defect, and FIG. 5C is a graph of the FFT as a function of time for a cylindrical rotation of 40°, again in the plane of the defect, the latter two rotations generating an additional peak at between 200 and 300 µs which changes position as the cylinder is rotated about its longitudinal axis of symmetry.

EXAMPLE 3

Figure 6:
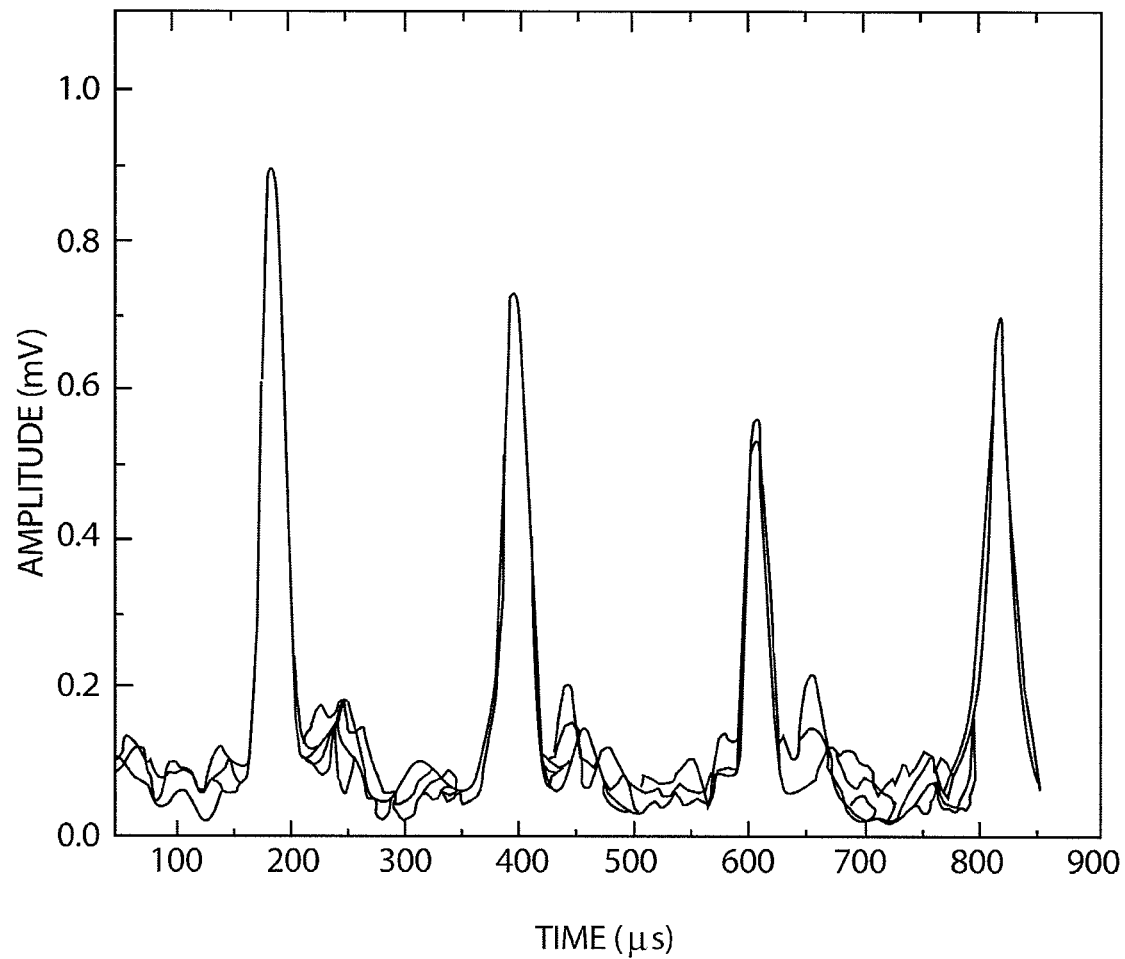
FIG. 6 is a graph of amplitude as a function of time showing measurement repeatability with respect to rotation of the pipe around stationary transducers between 180° and 240°, the transducers being further than 3 in. away from the defect along the longitudinal axis of the pipe, the defect having a depth of 20% of the wall thickness, and indicates that the pipe wall is homogeneous.

FIG. 6 is a graph of amplitude as a function of time showing measurement repeatability with respect to rotation of the pipe around stationary transducers between 180° and 240° and further than 3 in. away from the defect having a depth of 20%, and indicates that the pipe wall is homogeneous.

EXAMPLE 4

Figure 7:
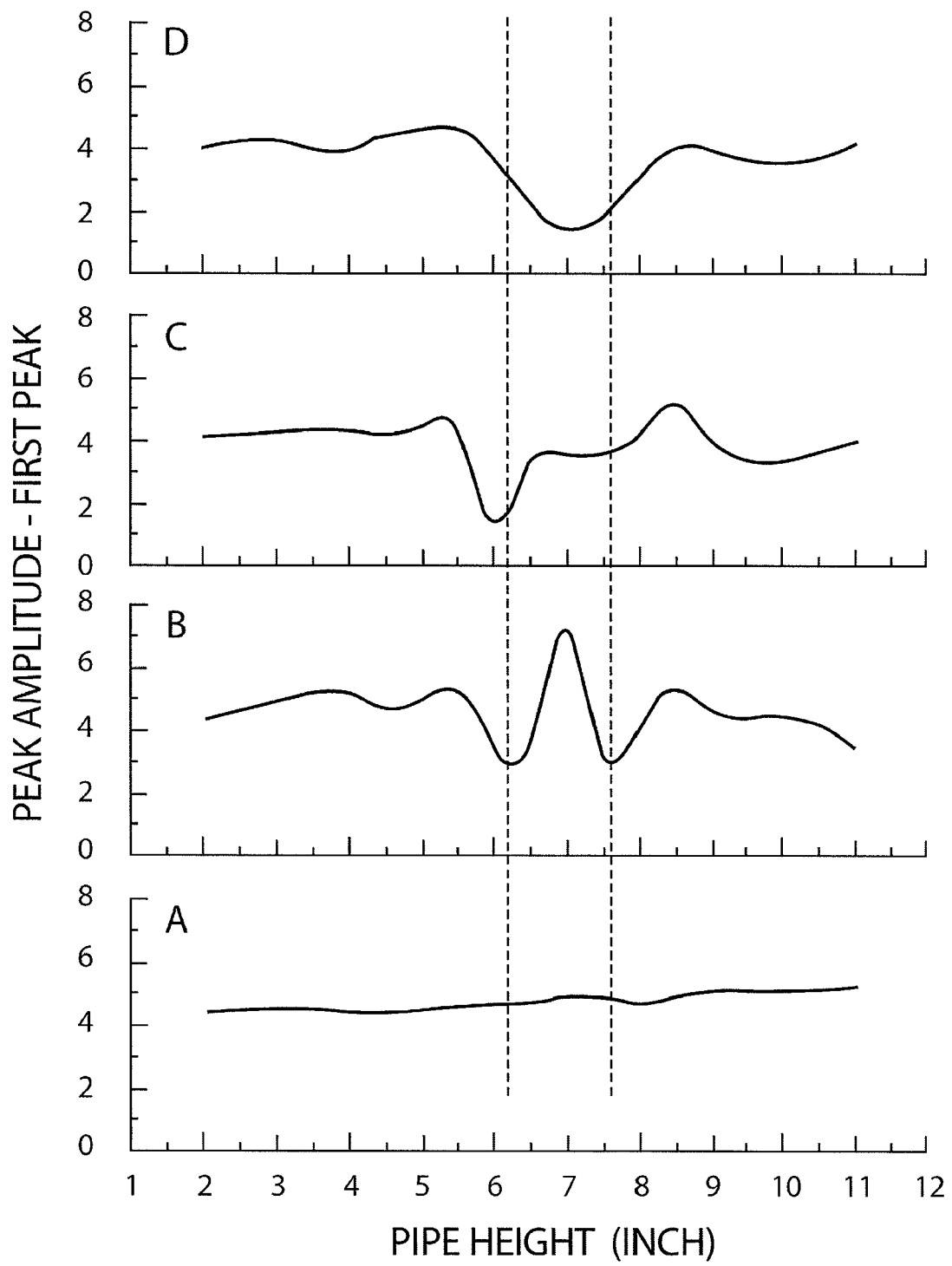
FIGS. 7A-7D are graphs of peak amplitude as a function of longitudinal distance along a pipe having a defect located at 7 in. from one end of a thin-walled (0.188 in.), 14 in. long steel pipe as the pipe is moved in the longitudinal direction along its length, with FIG. 7A showing a curve having no defect.

FIGS. 7A-7D are graphs of peak amplitude as a function of longitudinal distance along a pipe having a defect located at 7 in. from one end of a thin-walled (0.188 in.), 14 in. long pipe as the pipe is moved in the longitudinal direction along its length, with FIG. 7A showing a curve having no defect; FIG. 7B showing a curve for a defect having a depth of 20% of the wall thickness on the outside thereof; FIG. 7C showing a curve for a defect having a depth of 50% on the outside thereof; and FIG. 7D showing a curve for a defect having a depth of 80% on the outside thereof, the transducers being located about 180° apart as shown in FIG. 5 hereof and facing the inside surface of the cylinder, with the defects located on the outside wall at approximately 90°.

The shapes of the curves in the region of the defect is likely due to a combination of factors: (1) interference of the ultrasound beam from various parts of the defect due to the large size of the defect when compared with the wavelength of the Lamb waves; and (2) mode conversion of the sound waves (different speeds) due to the dissimilar wall thicknesses, the two different thicknesses placing the measurement range at different locations on the sound dispersion curves.

EXAMPLE 5

Figure 8A:
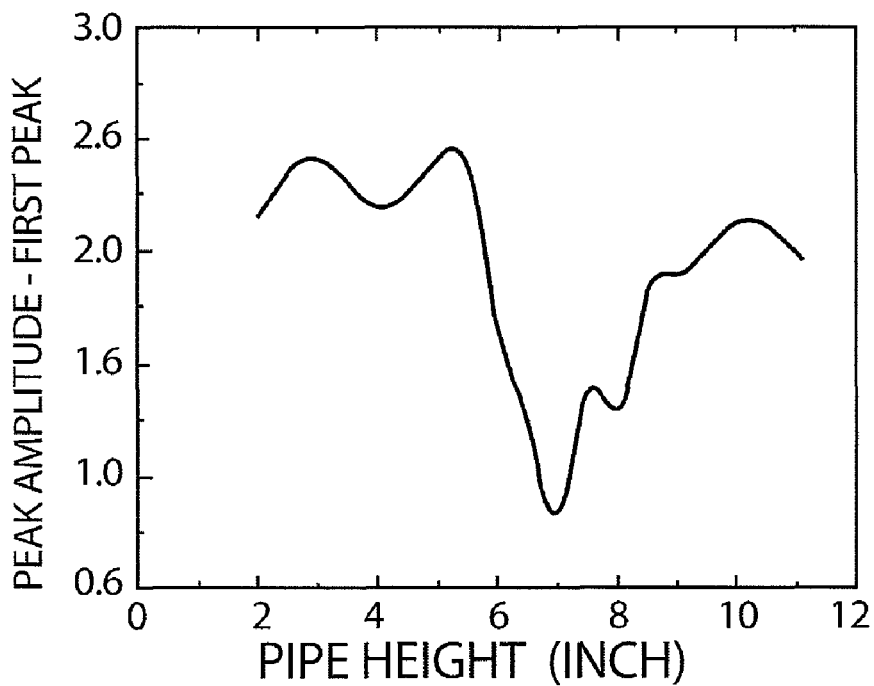
FIGS. 8A and 8B are graphs of the peak amplitude as a function of the length along the longitudinal axis of pipe (in.), showing results obtained when the outer pipe surface is completely covered with fiberglass adhesive tape (FIG. 8A), and when a 2 in. band of fiberglass adhesive tape covers the defect in the outer wall of the pipe (FIG. 8B).
Figure 8B:
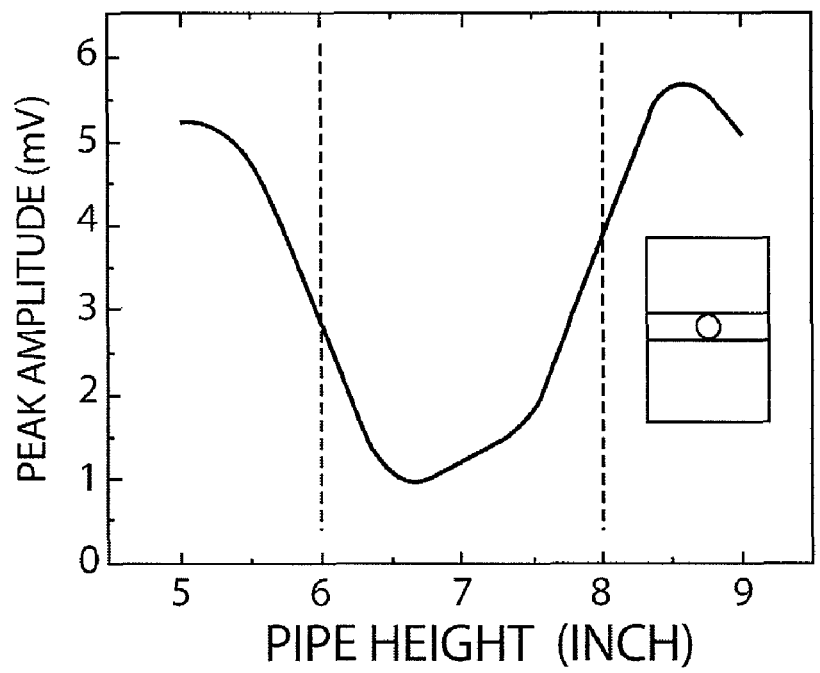

It is of interest in the application of the present invention how coatings (for example, paint, etc.) on the surfaces of the wall of a pipe affect the measurements. Since paints permanently alter the surfaces of pipes, strong adhesive tapes were used. Simple tapes did not have much of an affect except for slight changes in signal amplitude. Glass fiber embedded tape with strong adhesive was tested. This tape has a 2 in. width and was wrapped around the pipe. Two tests were performed: (1) the width of the defect was covered with the tape as well as the remaining circumference of the pipe in the vicinity of the plane of the defect; and (2) the entire outer surface of the pipe was covered. FIGS. 8A and 8B are graphs of the peak amplitude as a function of the length along the longitudinal axis of pipe (in.), showing results obtained when the outer surface of the pipe was completely covered with tape (FIG. 8A), and when the 2-in. band of fiberglass adhesive tape covered the defect and the surface of the pipe in the vicinity of the defect (FIG. 8B). Since the wavelength of the Lamb waves is smaller than the size of the defect generated on the pipe surface, scattering from different portions of the defect interfere at the receiver and produce effects that are different than in the absence of scattering.

The EXAMPLES illustrate that defects can be detected, and that each defect depth has a different characteristic. Rotation of the defect with respect to the position of the transducers verifies that the defects can be detected and quantified regardless of the defect position on the pipe surface. It was also found that when a defect is closer to the transmitter, the received signal is significantly enhanced as compared to when the defect is closer to the receiver. Further, the present apparatus (with both transducers on the inside) readily detected a cluster of ten pits randomly distributed in the area of a circle about 2 cm in diameter in the inner surface of a steel, 8 in. diameter pipe having a wall thickness of 0.19 in., each pit being 2 mm in diameter and having a depth of 50% of the wall thickness.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for non-contact detection of features in or on the wall of a hollow pipe having a longitudinal axis, the wall having an inner surface, comprising in combination:
   an air-coupled transmitting transducer disposed within said hollow pipe for generating ultrasonic waves at a first chosen angle to the normal to the inner surface of the wall, at a chosen first distance from the surface, and at a chosen longitudinal distance along the axis;
   a sweep generator for exciting said air-coupled transmitting transducer over a selected frequency range, whereby Lamb waves are generated in the wall of said pipe;
   an air-coupled receiving transducer disposed within said hollow pipe at the same longitudinal position as said transmitting transducer, at a second chosen angle to the normal to the inner surface of the wall and at a second chosen distance from the inner surface of the wall, for receiving ultrasonic waves emitted by the inner surface of said wall, said receiving transducer producing an electrical signal in response to the ultrasonic waves received thereby;
   a narrow-band tracking filter for receiving the electrical signal from said receiving transducer at the excitation frequency in the selected frequency range and generating a noise-filtered signal therefrom; and
   a signal processor for receiving the noise-filtered signal from said narrow-band tracking filter and producing a signal containing amplitude and phase information from the Lamb waves in the frequency domain.

2. The non-contact detection apparatus of claim 1, further comprising an apparatus for receiving the signal from said signal processor in the frequency domain and transforming the signal into the time domain by Fast Fourier Transform.

3. The non-contact detection apparatus of claim 1, wherein the first chosen and the second chosen angle are between about 4° and about 10°.

4. The non-contact detection apparatus of claim 1, wherein said detection apparatus is mounted on a frame that can be moved along the axis through the inside of said hollow pipe.

5. The non-contact detection apparatus of claim 1, wherein the first chosen distance from the inner surface of the wall of said pipe and the second chosen distance from the inner surface of the wall of said pipe are greater than 1 cm.

6. The non-contact detection apparatus of claim 1, wherein said hollow pipe is adapted to carry gases.

7. A method for non-contact detection of features in or on the wall of a hollow pipe having a longitudinal axis, the wall having an inner surface, comprising the steps of:
   generating ultrasonic waves having a chosen frequency in a selected frequency range at a chosen angle to the normal to the inner surface, from a first chosen distance therefrom, and at a chosen longitudinal distance along the axis, whereby Lamb waves are generated in the wall of the pipe;
   sweeping the generated ultrasonic waves over the selected frequency range;
   detecting ultrasonic waves emitted by the inner surface of the wall of the pipe at a second chosen angle to the normal to the inner surface and at a second chosen distance therefrom;
   producing a signal from the detected ultrasonic waves; and
   generating a narrow-band, noise-filtered signal at each frequency from the signal whereby a signal containing amplitude and phase information from the Lamb waves is generated in the frequency domain.

8. The method of claim 7, further comprising the step of transforming the signal into the time domain by Fast Fourier Transform.

9. The method of claim 7, wherein the first chosen angle and the second chosen angle are between about 4° and about 10°.

10. The method of claim 7, wherein the first chosen distance from the inner surface of the wall of the pipe and the second chosen distance from the inner surface of the wall of the pipe are greater than about 1 cm.

11. The method of claim 7, wherein the hollow pipe is adapted to carry gases.

12. The method of claim 7, wherein said step of generating ultrasonic waves having a chosen frequency is achieved using an air-coupled transmitting transducer disposed within the hollow pipe excited by a sweep generator, and said step of detecting ultrasonic waves emitted by the inner surface of the wall is achieved using an air-coupled receiving transducer disposed within said hollow pipe at the same longitudinal position as the transmitting transducer.

13. The method of claim 12, wherein the transmitting transducer and the receiving transducer are mounted on a frame that can be moved along the axis through the inside of the hollow pipe.

14. Apparatus for non-contact detection of features in or on the wall of a hollow pipe having a longitudinal axis, the wall having an outer surface, comprising in combination:
   an air-coupled transmitting transducer disposed outside of said hollow pipe for generating ultrasonic waves greater than 100 kHz at a first chosen angle to the normal to the outer surface, at a chosen first distance from the surface and at a first chosen longitudinal distance along the axis;
   a sweep generator for exciting said air-coupled transmitting transducer over a selected frequency range, whereby Lamb waves are generated in the wall of said pipe;
   an air-coupled receiving transducer disposed outside of said hollow pipe at approximately the same longitudinal position as said transmitting transducer, at a second chosen angle to the normal to the outer surface and at a second chosen distance therefrom, for receiving ultrasonic waves emitted by the outer surface of said wall, said receiving transducer producing an electrical signal in response to the ultrasonic waves received thereby;
   a narrow-band tracking filter for receiving the electrical signal from said receiving transducer at the excitation frequency in the selected frequency range and generating a noise-filtered signal therefrom; and
   a signal processor for receiving the noise-filtered signal from said narrow-band tracking filter and producing a signal containing amplitude and phase information from the Lamb waves in the frequency domain.

15. The non-contact detection apparatus of claim 14, further comprising an apparatus for receiving the signal from said signal processor in the frequency domain and transforming the signal into the time domain by Fast Fourier Transform.

16. The non-contact detection apparatus of claim 14, wherein the first chosen angle and the second chosen angle are between about 4° and about 10°.

17. The non-contact detection apparatus of claim 14, wherein the first chosen distance from the outer surface of the wall of said pipe, and the second chosen distance from the outer surface of the wall of said pipe, are greater than about 1 cm.

18. The non-contact detection apparatus of claim 14, wherein said hollow pipe is adapted to carry gases.

19. A method for non-contact detection of features in or on the wall of a hollow pipe having a longitudinal axis, the wall having an outer surface, comprising the steps of:
generating ultrasonic waves having a chosen frequency in a selected frequency range greater than 100 kHz at a first chosen angle to the normal to the outer surface from a first chosen distance from the surface and at a chosen longitudinal distance along the axis, whereby Lamb waves are generated in the wall of the pipe;
sweeping the generated ultrasonic waves over the selected frequency range;
detecting ultrasonic waves emitted by the outer surface of the wall of the pipe at a second chosen angle to the normal to the outer surface and at a second chosen distance therefrom;
producing a signal from the detected ultrasonic waves; and
generating a narrow-band, noise-filtered signal at each frequency from the signal;
whereby a signal containing amplitude and phase information from the Lamb waves is generated in the frequency domain.

20. The method of claim 19, further comprising the step of transforming the signal into the time domain by Fast Fourier Transform.

21. The method of claim 19, wherein the first chosen angle and the second chosen angle are between about 4° and about 10°.

22. The method of claim 19, wherein the first chosen distance from the outer surface of the wall of the pipe and the second chosen distance from the outer surface of the wall of the pipe are greater than about 1 cm.

23. The method of claim 19, wherein the hollow pipe is adapted to carry gases.

24. The method of claim 19, wherein said step of generating ultrasonic waves having a chosen frequency is achieved using an air-coupled transmitting transducer disposed outside of the hollow pipe excited by a sweep generator, and said step of detecting ultrasonic waves emitted by the inner surface of the wall is achieved using an air-coupled receiving transducer disposed outside of the hollow pipe at the same longitudinal position as the transmitting transducer.

* * * * *

UNITED STATES PATENT AND TRADEMARK OFFICE
CERTIFICATE OF CORRECTION

PATENT NO.        : 7,963,165 B2
APPLICATION NO.   : 11/861229
DATED             : June 21, 2011
INVENTOR(S)       : Dipen N. Sinha It is certified that error appears in the above-identified patent and that said Letters Patent is hereby corrected as shown below:

Title Page, Item (74) Attorney, Agent, or Firm,

"Samual M. Freund" should read

-- Samuel M. Freund --.

Signed and Sealed this
First Day of May, 2012

David J. Kappos
*Director of the United States Patent and Trademark Office*